United States Patent [19]
Hausheer et al.

[11] Patent Number: 5,789,000
[45] Date of Patent: Aug. 4, 1998

[54] STERILE AQUEOUS PARENTERAL FORMULATIONS OF CIS-DIAMMINE DICHLORO PLATINUM

[75] Inventors: Frederick H. Hausheer; Kochat Haridas; Dhanabalan Murali; Dasharatha Gauravaram Reddy; Peddaiahgari Seetharamulu, all of San Antonio, Tex.

[73] Assignee: Bionumerik Pharmaceuticals, Inc., San Antonio, Tex.

[21] Appl. No.: 338,379

[22] Filed: Nov. 14, 1994

[51] Int. Cl.$^6$ .................... A61K 33/24; A61K 31/505; A61K 31/44
[52] U.S. Cl. .................... 424/649; 514/274; 514/283
[58] Field of Search .................... 424/10, 649; 514/274, 514/283

[56] References Cited

FOREIGN PATENT DOCUMENTS 0 538 858 A1  4/1993  European Pat. Off. .

OTHER PUBLICATIONS

Arrick, Bradley A., et al. *Glutathione Metabolism as a Determinant of Therapeutic Efficacy: A Review.* Cancer Research, 44: 4224–4232, Oct. 1984.

Andrews, Paul A., et al. *Metallothionein–mediated cisplatin resistance in human ovarian carcinoma cells.* Cancer Chemother Pharmacol, 19: 149–154, 1987.

Bajorin, Dean F., et al. *Pharmacokinetics of cis–Diamminedichloroplatinum(II) after Administration in Hypertonic Saline.* Cancer Research, 46: 5969–5972, Nov. 1986.

Borch, Richard F., et al. *Effect of diethyldithiocarbamate rescue on tumor response to cis–platinum in a rat model.* Proc. Natl. Acad. Sci. USA, 77: 5441–5444, Sep. 1980.

Brock, N., *The Development of Mesna for the Inhibition of Urotoxic Side Effects of Cyclophosphamide, Ifosfamide, and Other Oxazaphosphorine Cytostatics.* Rec. Res. Cancer Res., 74: 270–278, 1980.

Brock, Norbert, et al., *Studies on the Urotoxicity of Oxazaphosphorine Cytostatics and its Prevention.* Eur. J. Cancer Clin. Oncol., 17: 1155–1163, 1981.

Brock, Norbert, et al., *Studies on the Urotoxicity of Oxazaphosphorine Cytostatics and its Prevention—III. Profile of Action of Sodium 2–mercaptoethane Sulfonate (Mesna).* Eur. J. Cancer Clin. Oncol., 18(12): 1377–1387, 1982.

Brock, N., et al. *Pharmacokinetcis and Mechanism of Action of Detoxifying Low–Molecular–Weight Thiols.* J. Cancer Res. Clin. Oncol., 108: 87–97, 1984.

Brock, Norbert, et al., *The develpoment of mesna for regional detoxification.* Cancer Treatment Reviews, 10(Suppl. A): 33–43, 1983.

Burkert, Hans, et al., *Clinical overview of mesna.* Cancer Treatment Reviews, 10(Suppl. A): 175–181, 1983.

Burkert, H., et al., *Bioavailability of Orally Administered Mesna.* Arzneim.–Forsch./Drug Res., 34;(II), 1597–1600, 1984.

Campbell, A. Bruce, et al., *Plasma Platinum Levels: Relationship to Cisplatin Dose and Nephrotoxicity.* Cancer Treatment Reports, 67(2): 169–172, Feb. 1983.

Choie, D. David, et al., *Acute and Chronic Cisplatin Nephropathy in Rats.* Laboratory Investigation, 44(5): 397–402, 1981.

Daugarrd, Gedske, et al., *Cisplatin nephrotoxicity A review.* Cancer Chemother. Pharmacol., 25:1–9, 1989.

DeConti, Ronald C., et al., *Clinical and Pharmacological Studies with cis–Diamminedichloroplatinum(II).* Cancer Research, 33: 1310–1315, Jun. 1973.

Dentino, Mariellen, et al., *Long Term Effect of Cis–Diamminedichloride Platinum (CDDP) on Renal Function and Structure in Man.* Cancer, 41(4): 1274–1281, Apr. 1978.

Earhart, Robert H., *Instability of cis–Dichlorodiammineplatinum in Dextrose Solution.* Cancer Treatment Reports, 62(7): 1105–1106, Jul. 1978.

Eastman, Alan, *Glutathione–mediated activation of anticancer platinum(IV) complexes.* Biochemical Pharmacology, 36(23): 4177–4178, 1987.

Eastman, Alan, *Reevaluation of Interaction of cis–Dichloro(ethylenediamine)platinum(II) with DNA.* Biochemistry, 25: 3912–3915, 1986.

Glover, Donna, et al., *WR–2721 and High–Dose Cisplatin: An Active Combination in the Treatment of Metastatic Melanoma.* Journal of Clinical Oncology, 5(4): 574–578, Apr. 1987.

Goldstein, Robin S., et al., *The Nephrotoxicity of Cisplatin.* Life Sciences, 32: 685–690, 1983.

Gonzalez–Vitale, Juan C., et al., *The Renal Pathology in Clinical Trials of Cis–Platinum(II) Diamminedichloride.* Cancer, 39: 1362–1371, 1977.

Hayes, Daniel M., et al., *High Dose Cis–Platinum Diammine Dichloride, Amelioration of Renal Toxicity by Mannitol Diuresis.* Cancer, 39: 1372–1381, 1977.

Howell, Stephen B., et al., *Intraperitoneal Cisplatin with Systemic Thiosulfate Protection.* Annals of Internal Medicine, 97: 845–851, 1982.

Hegedüs, L., et al., *Chemical reactivity of cisplatin bound to human plasma proteins.* Cancer Chemother. Pharmacol., 20: 211–212, 1987.

Jacobs, Charlotte, et al., *Renal Handling of Cis–Diamminedichloroplatinum(II).* Cancer Treatment Reports, 64(12): 1223–1226, Dec. 1980.

James, C.A., et al., *Estimation of mesna and dimesna in plasma and urine by high–performance liquid chromatography with electrochemical detection.* Journal of Chromatography, 382: 394–398, 1986.

(List continued on next page.)

Primary Examiner—Jerome D. Goldberg
Attorney, Agent, or Firm—Fish & Richardson, P.C.

[57] ABSTRACT

This invention describes a novel formulation containing both cis-diammine dichloro platinum and a water soluble disulfide, 2,2'-dithio-bis-ethane sulfonate in the same solution, wherein the presence of the disulfide and the parenteral administration of the formulation reduces the risk of cisplatin induced nephrotoxicity when treating human patients with cancer.

3 Claims, 2 Drawing Sheets

OTHER PUBLICATIONS

Jocelyn, *Biochemistry of the SH Group*. Academic Press, London, New York, 1972.

Kelley, Susan L., et al., *Overexpression of Metallothionein Confers Resistance to Anticancer Drugs*. Science, 241: 1813–1815, Sep. 1988.

Kempf, S.R., et al., *Effective prevention of the nephrotoxicity of cis–platin (CDDP) by administration of sodium 2–mercaptoethane–sulfonate (MESNA) in rats*. Br.J. Cancer, 52:937–939, 1985.

Kociba, Richard J., et al., *Acute Toxicologic and Pathologic Effects of Cis–Daimminedichloroplatinum (NSC–119875) in the Male Rat*. Cancer Chemotherapy Reports, 55: 1–8, Feb. 1971.

Lemaire, Henry, et al., *The Synthesis of 2–Mercaptoethane–sulfonamide*. J. Org. Chem., 26: 1330–1331, Apr. 1961.

Markman, Maurie, *Intraperitoneal Chemotherapy*. Seminars in Oncology, 18(3): 248–254, Jun. 1991.

Leonard, B.J., et al., *Antileukaemic and Nephrotoxic Properties of Platinum Compounds*. Nature, 234: 43–45, Nov. 1971.

Offerman, Joop J.G., et al., *Acute effects of cis–diamminedichloroplatinum (CDDP) on renal function*. Cancer Chemother. Pharmacol., 12: 36–38, 1984.

Ormastad, Kari, et al., *Pharmacokinetcis and Metabolism of Sodium 2–Mercaptoethanesulfonate in the Rat*. Cancer Research, 43: 333–338, Jan. 1983.

Ostrow, S., et al., *High–Dose Cisplatin Therapy Using Mannitol Versus furosemide Diuresis: Comparative Pharmacokinetics and Toxicity*. Cancer Treatment Reports, 65:73–78, 1981.

Ozols, Robert F., et al., High–Dose Cisplatin in Hypertonic Saline. Annal s of Internal Medicine, 100: 19–24, 1984.

Pfeifle, Craig E., et al., *High–Dose Cisplatin with Sodium Thiosulfate Protection*. Journal of Clinical Oncology, 3(2): 237–244, Feb. 1985.

Pinto, Ann L., et al., *Binding of the Antitumor Drug cis–Diamminedichloroplatinum(II) (Cisplatin) to DNA*. Biochmica et Biophysica Acta., 780: 167–180, 1985.

Perry, M.C., *The Chemotherapy Source Book*, Williams and Wilkins, 1172 pp., 1992.

Reed, Eddie, et al., *Platinum Analogues in Cancer Chemotherapy*, Principles and Practice, 465–490, 1990.

Rosenberg, Barnett, et al., *Platinum Compounds: a New Class of Potent Antitumor Agents*. Nature, 222: 385–386, Apr. 1969.

Rozencweig, Marcel, et al., *Cis–diamminedichloroplatinum (II) A New Anticancer Drug*. Annals of Internal Medicine, 86: 803–812, 1977.

Safirstein, Robert, et al., *Cisplatin Nephrotoxicity*. American Journal of Kidney Diseases, 8(5): 356–367, Nov. 1986.

Sidau, Beate, et al., Determination of sodium 2–mercaptoethanesulphonate by high–performance liquid chromatography using post–column reaction colorimetry or electrochemical detection. Journal of Chromatography, 311: 234–238, 1984.

Symposium: *Cisplatin: Contemporary Treatment Approaches*. Seminars in Oncology, 16(Suppl. 6): 1–128, 1989.

Thomson, A.J., *The Interactions of Platinum Compounds with Biologial Molecules* . Rec. Res. Cancer Res., 48: 38–62, 1974.

Shaw, I.C. and Weeks, M.S., Excretion of Disodium Bis–2–Mercaptoethanesulphonate (Dimesna) in the Urine of Volunteers after Oral Dosing; Eur J Cancer Clin Oncology 23:933–935; 1987.

Levine, Barry S., Henry, Mary C., Port Curtis D., Richter, Ward R., and Urbanek, Mary A.; Nephrotoxic Potential of cis–Diamminedlchloroplatinum and Four Analogs In Male Fischer 344 Rats; JNCI, 67(1):201–206 Jul. 1981.

Brock et al., Arzwem Forsett 32:486–487 (1982) Abstract Only.

Pohl et al., Meth. Fiwd. Clin. Pharmacol. 3(Supp.1): 95: 101, 1981 Abstract only.

Leeuwenkamp, OR., van der Vijgh, W.J.F., Neijt, J.P., and Pinedo, H.M., *Reaction kinetics of cisplatin and its monoaquated species with the (potential) renal protecting agents (di)mesna and thiosulfate*. Cancer Chemother.Pharmacol., 27(2):112–114, 1990.

Leeuwenkamp, O.R., Neijt, J.P., van der Vijgh, W.J.F., and Pinedo, H.M., *Reaction Kinetics of Cisplatin and its Monoaquated Species with the Modulating Agents (Di)mesna and Thiosulphate*. Eur J Cancer 27(10), 1243–1247, 1991.

Petru, E. and Schmahl, D., *Combination Effects in the Carcinogenesis of Cytotoxic Agents and its Possible Inhibition: Experimental and Clinical Results*. Combination Effects in Chemical Carcinogenesis, VCH Publishers: 153–173, 1988.

Brade, W., Seeber, S., and Herdrich, K. *Comparative activity of ifosfamide and cyclophosphamide*. Cancer Chemther Pharmacol (1986) 18 (Suppl 2): S1–S9.

Schoenike, S. E. and Dana, W.E. *Ifosfamide and mesna*. Clinical Pharmacy vol. 9, Mar. 1990: 179–191.

Mathur et al., 1980, Polymer as Aids in Organic Chemistry, Academic Press, New York, Ch. 9–12:138–197.

Needels et al., 1993, Proc. Natl. Acad. Sci. USA, 90:10700–10704 *Generation and screening of an oligonucleotide–encoded sythetic peptide library*.

Nikolaiev et al., 1993, Peptide Research, 6(3):161–170 *Peptide–encoding for structure determination of nonsequenceable polymers within libraries synthesized and tested on solid phase supports*.

Ohlmeyer et al., 1993, Proc. Natl. Acad. Sci. USA, 90:10922–10926 *Complex synthetic chemical libraries indexed with molecular tags*.

Tjoeng et al., 1990, Int. J. Pept. Protein Res. 35:141–146 *Multiple peptide synthesis using a single support (MPS3)*.

Van Brundt, Nov. 16, 1993, BioWorld Today pp. 3–5 *Affymax creates new large–scale drug screen*.

Van der Zee et al., 1989, Eur. J. Immonl. 19:43–48 *Efficient mapping and characterization of a T cell epitope by the simultaneous synthesis of multiple peptides*.

STERILE AQUEOUS PARENTERAL FORMULATIONS OF CIS-DIAMMINE DICHLORO PLATINUM

BACKGROUND OF THE INVENTION

1. Field of the Invention

This invention describes a novel aqueous formulation and methods of use thereof, of cis-diammine dichloro platinum and a water soluble disulfide, 2,2'-dithio-bis-ethane sulfonate and wherein the cis-diammine dichloro platinum and 2,2'-dithio-bis-ethane sulfonate are administered simultaneously to reduce the risk of cisplatin induced nephrotoxicity when treating human patients with cancer.

2. Description of the Related Art

A. Introduction

The use of cytotoxic anticancer drugs pose an increased risk of certain untoward side effects in human subjects undergoing cancer treatment. Drug toxicity associated with the use of anticancer drugs greatly limits their clinical utility and safety in human subjects. For example, drug induced impairment of cellular and/or organ functions may result in organ-specific toxicities in human subjects being treated for cancer. Additionally, the drugs themselves or their metabolites may accumulate or damage certain cellular components or impair certain biochemical reactions in specific organs. The toxicities observed due to the administration of anticancer drugs are usually dose dependent (e.g., busulfan induced myelosuppression), are often related to cumulative dosages administered (e.g., BCNU induced pulmonary toxicity; anthracycline induced cardiac toxicity), and idiosyncratic drug toxicities are noted with some frequency with certain anticancer drugs (e.g., mitomycin-C induced hemolytic uremic syndrome). By impairing or damaging normal cellular function in specific organs the anticancer drug is causally connected with the drug-induced organ damage.

As a result of drug induced toxicity associated with the administration of anticancer drugs to humans, clinicians attempt to prevent or reduce the risk of drug toxicity by certain pharmacologic maneuvers. Such clinical maneuvers can impose risk of additional side effects, or result in a dose reduction of the anticancer drug which in turn may adversely affect the likelihood of achieving control of the patient's tumor. If the major dose-limiting organ toxicity of a particular anticancer drug is eliminated or substantially reduced, the result is that the safety and efficacy of the primary anticancer drug is greatly increased. A significant reduction in drug toxicity in cancer treatment generally results in greater ability to administer higher doses of the drug, prevents or reduces the number of treatment delays, and increases the safety and the quality of life for patients. An example of this approach is the use of G-CSF to reduce the duration and magnitude of drug induced myelosuppression resulting from the administration of several different types of anticancer drugs. Therefore, an important area of drug research and treatment is aimed at developing new methods to prevent or reduce drug induced dose limiting toxicities in human cancer patients.

This invention teaches novel, aqueous, sterile parenteral formulations of cis-diammine dichloro platinum using the water soluble disulfide 2,2'-dithio-bis-ethane sulfonate for the purpose of treating patients with cancer and reducing the risk of cisplatin induced nephrotoxicity. This invention also teaches methods of manufacture and use of formulations containing cis-diammine dichloro platinum and disulfide 2,2'-dithio-bis-ethane sulfonate.

B. Cis-Diammine Dichloro Platinum

(1) Background of Cis-Diammine Dichloro Platinum

Cis-diammine dichloro platinum (hereinafter referred to as "cisplatin" or "CDDP") is a widely used anticancer drug which is used in combination with other anticancer drugs in the treatment of cancers of the lung, head and neck, ovary, esophagus, bladder, and testis. Along with its potent anticancer properties, cisplatin also has demonstrated clinically significant toxicities which limit its clinical utility and pose certain risks to patients undergoing treatment for certain types of cancer. The therapeutic benefits must always be carefully weighed against the possibility of these significant drug related toxicities associated with the use of cisplatin . It is well known that one of the most important and common dose limiting toxicities of cis-diammine dichloro platinum is renal damage in patients receiving this drug for treatment of their cancer (Perry, M. C., The Chemotherapy Source Book, Williams and Wilkins, 1172 pp., 1992).

A stable and sterile aqueous solution of cisplatin in a sealed ampoule or vial containing a unit dosage form suitable for intravenous administration to a human patient with cancer was described in U.S. Pat. No. 4,310,515, entitled "Pharmaceutical Compositions of Cisplatin" (Issued Jan. 12, 1982). The patent claims cisplatin provided in a concentration between about 0.1 and about 1.0 mg/ml and a pH in a range of 2.0 to 3.0. The sterile aqueous cisplatin solution may also contain sodium chloride and mannitol. In comparison, the subject matter of the claimed invention is directed to a formulation of cisplatin (in a concentration of 0.1 to 1.0 mg/ml) and 2,2'-dithio-bis-ethane sulfonate (pH in the range of 2.0 to 6.0).

(2) Mechanisms of Action of Cis-Diammine Dichloro Platinum

Cisplatin exchanges chloride ions for nucleophilic groups such as $RS^-$, $R-S-CH_3$, imidazole nitrogens and $R-NH_2$ to form linkages which can be very stable. In an aqueous solution, one or both chloride ions may be replaced by water to produce a hydrated intermediate known as an "aquo cisplatin" species (See Reactions 1 and 2 below). The water molecule(s) attached to the cisplatin can be subsequently eliminated by an incoming nucleophile. In some cases there can be direct displacement of the chloride ion by an incoming nucleophile without the participation of the solvent. Thus, several species of cisplatin ("Pt") exist in solution as defined according to the following equilibria:

Reaction 1 $Pt(NH_3)_2Cl_2 + H_2O \rightarrow [Pt(NH_3)_2Cl(H_2O)]^+$ 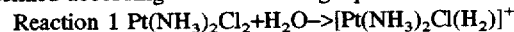

Reaction 2 $[Pt(NH_3)_2Cl(H_2O)]^+ + H_2O \rightarrow [Pt(NH_3)_2(H_2O)_2]^{++}$ 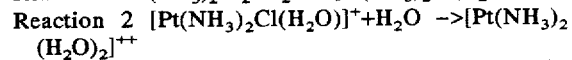

The addition of chloride ions to the medium shifts the equilibrium to the left and the reactivity of the cisplatin species depends on the chloride concentration of the medium. Isotonic and hypertonic saline solutions have high chloride ion concentrations and cisplatin will predominate as the $Pt(NH_3)_2Cl_2$ species. The displacement of chloride ions from $Pt(NH_3)_2Cl_2$ in an environment with a high chloride concentration occurs very slowly over time with exposure to the strongest nucleophiles, such as the sulfur anion. For example, formulation of cisplatin with sodium thiosulfate ($NaSO_3-S^-$) or 2-mercapto ethane sulfonate (mesna), is impractical because of the chemical quenching of cisplatin with the sulfur anion or the sulfhydryl moiety of thiosulfate and mesna, respectively. Cisplatin is also directly incompatible with diethyldithiocarbamate due to the presence of the sulfur anion, and thus cannot be formulated in the same solution for parenteral administration.

Cisplatin is believed to act on tumor cell DNA by forming intrastrand crosslinks of the drug attaching to the N7 atom of the imidazole between adjacent purine bases comprising predominantly sequences of 5'-GG-3', 5'-AG-3' or 5'-GXG-3' where X is a naturally occurring purine or a pyrimidine (e.g., adenine, thymine, cytosine or guanine; Eastman, A., Biochemistry, 25, 3912–3915, 1986; Pinto, A. L. and Lippard, S., Biochem. Biophy. Acta, 780, 167–180, 1985). Cisplatin is believed to exert its antitumor effects by the formation of intrastrand crosslinks which may result in alterations in DNA structure or function. In order for cisplatin to react with certain nucleic acid sequences in cellular DNA, it must first undergo chemical conversion to an active species by the displacement of chloride ligands with water to form the mono-aquo or di-aquo species. The aquo species of cisplatin is reactive with nucleophilic species, including the imidazole nitrogens on DNA or sulfhydryl groups which are also present in cells forming the renal tubular epithelium in humans.

Cisplatin readily reacts with compounds containing sulfhydryl moieties. Sulfhydryl groups are found in cysteine, glutathione, homocysteine. Metallothionein is a 7 kDa protein which has a high (approximately 30%) cysteine content (Kelly, S.L. et al., Science, 241, 1813–1815, 1988). Increased cellular concentrations of metallothionein and glutathione have been correlated with drug resistance to cisplatin therapy. Thus, if the local renal tubular concentration of sulfhydryl groups from 2-mercapto ethane sulfonate is increased, then cisplatin toxicity may be reduced by the chemical quenching of the cisplatin aquo species in the renal tubules. The present invention accomplishes this objective.

C. Orally or Parenterally Administered Mesna Forms Disulfide Conjugates with Cysteine, Homocysteine, and Glutathione in Human Subjects The inventors submit that parenterally or orally administered mesna does not undergo significant dimerization in the plasma of human subjects. The inventors also contend that mesna rapidly forms disulfides with cysteine, glutathione and homocysteine to a much larger extent (e.g. more than 95% of an administered dose of mesna). These mesna-cysteine, mesna-glutathione, and mesna-homocysteine disulfides are rapidly eliminated by the kidneys, mostly through glomerular filtration. However, because of the amino acid moiety, there may be some cellular uptake of these metabolites which in turn reduces the availability of free thiols in the kidney. In the renal tubule, mesna-cysteine, mesna-glutathione, and mesna-homocysteine disulfide conjugates are reduced by glutathione reductase and thiol transferase enzymes to form free thiols. The free thiols (e.g., mesna, cysteine, homocysteine and glutathione) react with and detoxify the aquo species of cisplatin in the renal tubules.

In the present invention, the chemical and pharmacologic behavior of parenterally or orally administered 2,2'- dithio-bis-ethane sulfonate is substantially different from the parenteral or oral administration of mesna as follows:

1. The 2,2'- dithio-bis-ethane sulfonate contained in the formulation remains intact in the plasma;
2. 2,2'-Dithio-bis-ethane sulfonate is a dianionic species and enters cells to a much lesser degree than mesna-cysteine, mesna-glutathione, and mesna-homocysteine disulfide conjugates. Therefore more disulfide is filtered and excreted via the renal route, making more thiols available for detoxification in the kidney relative to parenterally or orally administered mesna; and
3. In the kidney, 2,2'- dithio-bis-ethane sulfonate undergoes reduction by renal glutathione reductase and thiol transferase enzymes to form free 2-mercapto ethane sulfonate, which in turn reacts with aquo species of cisplatin resulting in renal excretion of non-toxic cisplatin-2-mercapto ethane sulfonate conjugates.

The claimed invention is in direct contrast to previously reported views of the pharmacology and metabolism of mesna. In FIG. 1, the previously reported views ("Old Hypothesis") is contrasted with the new hypothesis as presented by the inventors.

For the purposes of this invention, the simultaneous administration of cisplatin with 2,2'-dithio-bis-ethane sulfonate provides a physiologically safe source of additional sulfhydryl groups in the proximal and distal convoluted tubules to prevent renal toxicity. Unlike mesna, 2,2'-dithiobis-ethane sulfonate is chemically inert with respect to cis-diammine dichloro platinum, and thus is compatible in the claimed formulation.

It has been previously shown that oral or parenteral administration of mercapto ethane sulfonate (mesna) to mice, rats or humans results in spontaneous autooxidation of mesna to form 2,2'-dithio-bis-ethane sulfonate in the plasma (FIG. 1, "Old Hypothesis," Left-hand Column). James and Rogers reported an HPLC assay for plasma thiols using an electrochemical detector (James, C. A. and Rogers, Journal of Chromatography, 382, 394–398, 1986). The inventors submit that by using the method of James and Rogers, the detection and chemical characterization of dimesna (the putative human plasma metabolite of mesna) is indirect because this method can not chemically distinguish between dimesna, mesna-cysteine, and mesna-homocysteine conjugates. The HPLC method of James and Rogers involved the reduction of the samples by sodium borohydride and the samples were subsequently assayed for thiols. The difference in concentration from the unreacted initial sample and the sample that had been reacted with sodium borohydride was used to determine the amount of what was thought to be dimesna in the plasma. The inventors contend that sodium borohydride would react with mesna-mesna, mesna-cysteine, mesna-glutathione, mesna-homocysteine conjugates and thus, they submit that the method of James and Rogers fails to distinguish and quantitate the relative amounts of these entities which would form as a consequence of mesna metabolism. Other investigators rely on a similar or identical method as used by James and Rogers. All of these reports fail to mention or take into account the possibility of mesna forming a significant proportion of thiol conjugates with entities other than mesna, e.g., mesna-cysteine, mesna-glutathione, mesna-homocysteine. The inventors submit that the method of James and Rogers is ambiguous, imprecise and not capable of specifically identifying the disulfide conjugate formed.

The inventors also note that increased cysteine elimination in the urine has been reported in association with the administration of mesna to human subjects (Sidau, B. and Shaw, I. C., J. Chromatography, 311, 234–238, 1984). This observation indirectly supports the inventors' current hypothesis of disulfide conjugation of mesna with other thiols in the plasma (FIG. 1, "New Hypothesis", Middle Column). The enhanced cysteine elimination in urine, as reported by Sidau et al., can be explained by the current invention. The inventors contend that a disulfide linkage forms between mesna and cysteine in the plasma and reduction by glutathione reductase and thiol transferase of the mesna-cysteine conjugates occurs in the renal tubular system to generate free thiols. The free thiols are predicted to react with toxic aquo metabolites of cisplatin.

Thus, the inventors contend that the reported mesna metabolism and pharmacology in human subjects is incorrect on the basis of chemical, biochemical and thermodynamic data. The inventors further submit that the claimed invention provides greater utility and efficacy of using cis-diammine dichloro platinum for the treatment of human patients with cancer. By way of this disclosure, the inventors contend that the amount of mesna in the plasma of human subjects undergoing spontaneous autooxidation is exceedingly small (less than 5% of the total amount of mesna administered), and that mesna preferentially undergoes extensive chemical conjugation with cysteine and other similar amino acids containing thiols to form disulfide conjugates in the plasma. The inventors submit that mesna will largely undergo conjugation with cysteine alone, or with cysteine residues contained in glutathione, or with other cysteine thiol containing peptides, or with homocysteine in human plasma (FIG. 1, "New Hypothesis", Middle Column).

Thus, the inventors maintain that upon mesna administration, the formation of cysteine-mesna conjugates occurs to a much larger extent and that these heteroconjugates are much more stable than mesna-mesna homoconjugates. It is important to note that the mesna-thiol amino acid conjugates are also subject to cellular uptake due to the presence of the amino acid moiety (FIG. 1, "New Hypothesis", Middle Column). The cellular uptake of the mesna-thiol amino acid conjugates greatly reduces the amount of disulfide presented to the renal tubules, and thus reduces the amount of free thiols available for detoxification as a function of the total dose administered. Also, because of greater chemical stability, it is implicitly more difficult for mesna-cysteine conjugates to have their disulfide linkages reduced to form free thiols which in turn can conjugate with the toxic cisplatin drug metabolites. Thus, mesna-mesna conjugates are chemically more facile in forming free thiols than the mesna-cysteine conjugates.

In view of the above discussion, the inventors submit that concurrent administration of 2,2'-dithio-bis-ethane sulfonate with cisplatin is chemically and pharmacologically superior to using mesna because: (1) a greater amount of disulfides will be delivered to the renal tubular system whereupon these disulfides are available for reduction by glutathione reductase and thiol transferases to form the free thiol, 2-mercapto ethane sulfonate, and (2) a lower amount of energy is needed to reduce the 2,2'-dithio-bis-ethane sulfonate disulfide linkage which in turn will generate a greater amount of free thiols in the renal tubules whereupon these free thiols can react with the toxic aquo species of cisplatin The object of this invention is the concurrent, parenteral administration of a 2,2'-dithio-bis-ethane sulfonate and cisplatin formulation to human subjects with cancer (FIG. 1, "Present Invention", Right-hand Column). The following characteristics of 2,2'-dithio-bis-ethane sulfonate support its use in the present invention:

1. 2,2'-dithio-bis-ethane sulfonate will predominate in the plasma compartment.
2. 2,2'-dithio-bis-ethane sulfonate is an anionic species because it has two negatively charged oxygens. Because of this anionic characteristic, the molecule penetrates cell membranes very poorly.
3. The highly anionic nature and small molecular size of 2,2'-dithio-bis-ethane sulfonate are key properties which account for its rapid and nearly exclusive excretion in high concentrations through the kidney.
4. In the absence of any other treatment, 2,2'-dithio-bis-ethane sulfonate has reportedly been tested only once in normal human volunteers (Brock N., et al., J. Cancer Res. Clin. Oncol., 108, 87–97, 1984; Brock N., et al., Eur. J. Cancer Clin. Oncol. 18, 1377–1387, 1982; Brock, N. et al., Eur. J. Cancer Clin. Oncol. 17, 1155–1163, 1981). However, the investigators failed to confirm the chemical identity of the metabolites in the plasma and urine of the human subjects.

Cisplatin induced nephrotoxicity will be reduced because high local concentration of mesna is generated at the same region of the renal tubules where a high concentration of aquo species of cisplatin are formed.

This invention is also useful because the concurrent administration of 2,2'-dithiobis ethane sulfonate and cisplatin: (1) insures treatment compliance, (2) will reduce pharmacy preparation costs, (3) will reduce errors in prescribing both drugs, and (4) will reduce the amount of additional prophylactic maneuvers needed in order to reduce toxicity and avoid iatrogenic related complications (i.e. furosemide, or hypertonic saline administration as described above).

This invention reduces cisplatin induced nephrotoxicity by the parenteral coadministration of 2,2'-dithio-bis-ethane sulfonate and cis-diammine dichloro platinum. The 2,2'-dithio-bis-ethane sulfonate and cis-diammine dichloro platinum are in a sterile aqueous formulation suitable for administration to human subjects with cancer. As discussed above, parenteral formulation of mesna (mercapto ethane sulfonate sodium) or sodium thiosulfate with cisplatin is not practical because the sulfhydryl groups on mesna or the sulfate anion of sodium thiosulfate will react with cisplatin yielding inactive species of cisplatin.

Formulations of cisplatin and 2,2'-dithio-bis-ethane sulfonate must be maintained at a pH less than 7.0 and greater than 1.0 because of the need to prevent the formation of aquo species of cisplatin and also to prevent the formation of mesna which could subsequently react with cisplatin species. Another important component of this invention is the use of sufficiently high concentrations of NaCl (e.g., 0.9% or greater) and HCl because the stability of cisplatin is proportionally related to the chloride ion concentration of the solution.

It is therefore the object of this invention to describe a novel formulation which contains both cis-diammine dichloro platinum and the water soluble disulfide, 2,2'-dithio-bis-ethane sulfonate, in the same formulation wherein the thiol reduces the risk of cisplatin induced nephrotoxicity when treating human patients with cancer.

D. Nephrotoxicity Associated with Cis-Diammine Dichloro Platinum Administration

One of the most important limitations in the human clinical use of cisplatin is the nephrotoxicity which develops as a consequence of cumulative and dose dependent exposure to the drug, or which may occur in setting the administration of cisplatin to patients with renal insufficiency or co-administration of other nephrotoxic agents (e.g., aminoglycosides) (Rozencweig et al., 1977, cis-Dianmminedichloroplatinum (II), Ann. Intern. Med., 86, 803; Gonzalez-Vitale et al., 1977, The renal pathology in clinical trials of cisplatin (II) dianiminedichloride, Cancer, 39, 1362; Campbell et al., 1983, Plasma platinum levels: Relationship to cisplatin dose and nephrotoxicity, Cancer Treat. Rep., 67, 169; Offerman et al., 1984, Acutte effects of cis-diammine-dichloroplatinum (CDDP) on renal function, Cancer Chemother. Pharmacol., 12, 36).

The major clinical features of cisplatin induced nephrotoxicity include decreases in creatinine clearance, elevated creatinine, elevated BUN and hypomagnesemia. The dose limiting toxicity of cisplatin when administered as a single dose per cycle is nephrotoxicity. Nephrotoxicity associated with cisplatin administration may be related to the peak plasma concentration of the drug. Hyperuricemia and hypoalbuminemia are predisposing factors to cisplatin nephrotoxcity along with renal insufficiency, concomitant administration of other drugs, including aminoglycoside antibiotics and possibly by amphotericin B.

The mechanism for cisplatin induced toxicity, as submitted by the inventors, is based on the following conclusions: (1) Cisplatin is parenterally administered to human patients with cancer (patients and subjects are used interchangeably in this invention) and the concentration of chloride in the blood plasma is high relative to the intracellular concentration of chloride. (2) A higher concentration of chloride in the plasma provides conditions which largely favor the maintenance of the unreactive neutral dichloro species of cisplatin . (3) The neutral dichloro cisplatin species can enter cells, such as cancer cells, and because the chloride concentration inside of the cell is low, the conversion of cisplatin dichloro species to mono-aquo or di-aquo species is favored. (4) The aquo cisplatin species is then available to form coordinate chelate crosslinks with certain nucleic acids in cellular DNA. (5) The neutral dichloro species of cisplatin can also pass through the renal glomerulus and can also be secreted into the proximal convoluted tubule in the kidney. (6) The aquo cisplatin species formed in the plasma compartment can pass through the glomerulus and damage the proximal tubular epithelial cells. (7) The proximal and distal convoluted tubules are major histopathologic sites of cisplatin induced renal damage. (8) The dichloro cisplatin species can pass through the tubular region known as the loop of Henle, where in the ascending limb of the loop, chloride ions are normally pumped out of the tubular lumen into the renal interstitium. (9) This egress of chloride ions from the tubular lumen is important for creating conditions which favor cisplatin renal toxicity because the intratubular concentration of chloride is normally reduced in the ascending limb of the loop of Henle. (10) The lower intratubular concentration of chloride favors the generation of a greater intratubular concentration of the reactive cisplatin aquo species which can subsequently react with the tubular epithelial cells in the kidney. (11) The reaction of cisplatin in the proximal and distal tubular sites with the renal epithelial cells leads to toxicity by damaging the normal function of these cells. The partially protective effects against cisplatin renal toxicity observed with the administration of loop diuretics such as furosemide may act by inhibiting chloride ion transport out of the tubule, and is not solely due to a diuretic effect. (12) The resulting higher chloride concentration in the tubular lumen would protect the brush border epithelial cells (which contain DNA), surface proteins, and enzymes (which contain sulfhydryl groups) by producing conditions which would favor the predominance of the dichloro form of cisplatin.

Typical pathological changes in the kidneys after cisplatin application have been observed in laboratory animals and humans. (Kociba and Sleight, 1971, Acute toxicologic and-pathologic effects of cis-diammine dichloro platinum in the male rat, Cancer Chemother. Rep., 55, 1; Choie et al., 1981, Acute and chronic cisplatin nephropathy in rats, Lab. Invest., 44, 397; Goldstein and Gilbert, 1983, The nephrotoxicity of cisplatin, Life Sci., 32, 685). These cisplatin induced renal lesions are dose and time dependent, and are mainly localized in the outer stripe of the medulla of the kidney, which corresponds to the microscopic anatomic location of the glomerulus and convoluted tubules.

Thus, cisplatin induced nephrotoxicity usually occurs as a result of the cumulative and dose dependent exposure to the drug, or when administered to patients with renal insufficiency or when coadministered with another nephrotoxic agent (e.g., aminoglycosides). The dose limiting toxicity of cisplatin, when the drug is administered as a single dose per cycle, is nephrotoxicity which may be related to the peak plasma concentration of the drug itself.

Cisplatin induced nephrotoxicity is a clinically important problem associated with the use of the drug, and certain clinical maneuvers are generally employed in an attempt to reduce the risk of this complication. These prophylactic maneuvers include:

a. Parenteral administration of hypertonic (3%) NaCl; (Ozols et al., 1984, High-dose cisplatin in hypertonic saline, Ann. Intern. Med., 100, 19);

b. Parenteral administration of normal (0.9%) NaCl;

c. Mannitol diuresis (Hayes et al., 1977, High dose cisplatin dianimine dichloride, amelioration of renal toxicity by niannitol diuresis, Cancer, 39, 1372);

d. pre- and/or post treatment hydration (oral or parenteral);

e. forced diuresis by the administration of loop diuretics such as furosemide (Ostrow et al., 1981, High-dose cisplatin therapy using mannitol versus furosemide diuresis: comparative pharmacokinetics and toxicity, Cancer Treat. Rep., 65, 73); and f oral or parenteral administration of reduced thiols such as diethyldithiocarbamate (rodents), thiosulfate (humans), or 3-aminopropyl amino ethylphosphorothioic acid (WR-2721).

However, these maneuvers have certain drawbacks which (1) limit the practical use of cisplatin and (2) introduce additional definite risks for treatment related complications in patients undergoing treatment. For example, the administration of hypertonic saline (NaCl 3.0%) poses the risk of iatrogenic hypernatremia. Hypernatremia is a life threatening medical emergency which can be fatal, and the administration of hypertonic saline is contraindicated in patients with elevated serum sodium or patients with congestive heart failure. The administration of normal saline (NaCl 0.9%) in patients increases the risk of fluid overload in patients. The use of powerful loop diuretics to increase urine production by the kidney such as furosemide increase the iatrogenic risk of hypokalemia, hyponatremia, hypocalcemia, hypovolemia, metabolic alkalosis and hypochloremia. All of these conditions can be life threatening and in some cases are fatal.

It is important to note that these maneuvers aimed at prophylaxis of cisplatin nephrotoxicity require additional clinical services, additional patient monitoring (e.g., physicians, nurses, and pharmacists), and additional hospitalization expense. Additionally, since these prophylactic maneuvers (aimed at reducing the risk of nephrotoxicity) are separate from the administration of the drug (cis-diammine dichloro platinum), the patient runs the risk of experiencing additional toxicity due to the maneuver itself (e.g., fluid overload, congestive heart failure, hyperosmotic state, hypernatremia or by physician, nurse, pharmacist or support staff human error).

E. Water Soluble Thiols as Detoxifying Agents in the Kidney
  1. 2-Mercaptoethane Sulfonate Sodium or "Mesna"

Mesna is a pharmacologically safe thiol that has been used clinically in human subjects for approximately two decades. Mesna has been reported to be eliminated rapidly through the kidneys, accumulates in the urine and, unlike cysteine or N-acetyl cysteine, only slightly penetrates cellular membranes. In the rat, over 80% of the administered dose of mesna is reportedly recovered in the urine within three hours after intravenous administration (Pohl et al., Meth. Find. Clin. Pharmacol. 3(Suppl 1), 95–101, 1981).

For the purposes of the present invention, the inventors wish to point out that the analytical methods previously used to detect the presence of mesna metabolite in the plasma or in the urine in the studies are incapable of determining the chemical identity of the thiol (see discussion above). Mesna is widely used to reduce or prevent the risk of hemorrhagic cystitis to the uroepithilium which is associated with the use of certain oxazaphosphorine anticancer drugs which include cyclophosphamide, ifosfamide and trophosphamide. Mesna administered orally or parenterally to human subjects significantly reduces the incidence of uroepithelial toxicity in patients receiving therapy with these drugs. Oxazaphosphorine induced hemorrhagic cystitis can be a life threatening condition due to profuse bleeding from the uroepithelial surfaces involving the ureters, bladder and urethra.

It is especially important to note for the present invention that oxazaphosphorine induced uroepithilial toxicity is chemically, biochemically, anatomically and pathologically distinct from the renal toxicity which is observed with administration of cisplatin. It is also important to note that the organic chemical interactions of mesna with acrolein, the toxic species produced by the metabolism of anticancer oxazaphosphorines which directly damages the uroepithelium, is entirely different than the proposed inorganic chemical interactions which lead to detoxification of cisplatin by mesna.

Mesna disulfide, the only reported metabolite of mesna, is reportedly formed spontaneously by autooxidation. Mesna dimers (two mesna molecules covalently attached via a disulfide linkage) are reported to predominate in the blood. This mesna dimer metabolite is reportedly eliminated through the kidneys by glomerular filtration, being partly reduced to mesna during excretion (Brock, et al., Arzneim Forsch, 32, 486–487, 1982). Reportedly, an average of approximately 45% of the administered mesna dose is found in the urine in the form of mesna, the reactive thiol. The remainder found is reportedly the mesna metabolite, dimesna.

2. Bioavailability of Orally Administered Mesna

In 1984, Burkert et al. described the bioavailability of orally administered mesna (sodium 2-mercaptoethane sulfonate, Uromitexan; Burkert et al., Arzneim.-Forsch./Drug Res. 34, 1597, 1984). Previous experimental studies in rats had demonstrated that mesna was absorbed from the intestine following oral administration and that it passed unchanged through the hepatic vascular system (Brock et al., J. Cancer Res. Clin. Oncol. 108, 87 1984; Ormstad et al., Cancer Research, 43, 333, 1983). It was proposed that in the plasma, mesna was rapidly oxidized to disulfide dimesna and that the reaction occurs when mesna was injected intravenously. It was further proposed that after glomerular filtration, about 50% of dimesna was reduced to mesna in the renal tubular epithelium.

The inventors propose that it is unlikely that oral or parenterally administered mesna would necessarily be oxidized in the plasma to form significant quantities of dimesna (e.g., quantities greater than 5%). The inventors propose that the significant majority of mesna reacts with other plasma thiols to form conjugates with cysteine, glutathione and other thiol containing amino acids which are small enough to still undergo glomerular filtration and possibly tubular secretion and would be cleaved to form mesna (plus the free amino acid) in the tubular lumen. The inventors also specifically propose for the first time that mesna reacts with other thiols in the plasma such as cysteine, homocysteine, or the cysteine contained in glutathione (See above discussion). Since mesna forms a disulfide linkage with thiol containing amino acids or peptides, it could still be filtered by the glomerulus or secreted in the proximal tubule. The therapeutic disadvantage of these mesna-cysteine disulfide conjugates is that their disulfide linkages are chemically more stable than the 2,2'-dithio-bis-ethane sulfonate conjugate proposed in the present invention.

Burkert et al. (Burkert et al., Bioavailability of orally administered mesna, Arzneim-Forsch./Drug Res. 34, 1597, 1984) confirmed the established bioavailability of orally administered mesna with studies in healthy volunteers and patients with tumors. Burkert et. al. tested the oral administration of mesna (Uromitexan drink ampoules) in 18 healthy probands and in 5 tumor patients. Following a single oral administration of either 20 or 40 mg/kg mesna, approximately 52% of the dose was excreted in the urine as reactive thiol groups and the only metabolite of mesna, mesna disulfide or dimesna, comprised the remaining 48%. The experimental methods used to characterize mesna or dimesna in these studies are not conclusive in establishing with certainty the precise chemical identity of mesna or dimesna as urinary metabolites. It is far more likely that mesna was conjugated with certain thiols such as cysteine, homocysteine or glutathione. The key description used to characterize the identity of the putative dimesna metabolite by previous research groups is "thiol groups" which could also represent other amino acids.

This study also concluded that after intravenous injection of 20 mg/kg mesna, about 48% of the dose administered appeared as thiol groups in the urine. It took approximately 13 hours (20 mg/kg p.o.) or 18 hours (40 mg/kg p.o.) for the concentration to drop below the minimum concentration presumed to still be protective (100 ug/ml). However, the elimination pattern and the time required to reach the threshold concentration of mesna varies dramatically from patient to patient.

3. Concomitant Use of Oral Mesna in Rats or Thiosulfate in Humans to Reduce the Urotoxic Effects of the Cisplatin Kempf et al. studied the effects of per os administration of sodium 2-mercaptoethane-sulfonate (mesna) in rats to prevent the nephrotoxic effects of cisplatin administered intraperitoneally (Kempf et al., Effective prevention of the nephrotoxicity of cisplatin (CDDP) by administration of sodizm 2-mercaptoethane-sulfonate (mesna) in rats, Br. J. Cancer, 52, 937–939, 1985). As described above, mesna is extensively used in patients who receive oxazaphosphorine antitumor drugs such as cyclophosphamide and ifosfamide to protect the urinary tract, especially the bladder, against the toxic metabolite, acrolein (Brock, et al., Arzneim Forsch, 32, 486–487, 1982). In the case of oxazaphosphorines, acrolein is produced as a result of their metabolism and mesna undergoes addition to the double bond of acrolein, resulting in a stable thioether adduct which has no damaging effects on the uroepithelium and is excreted in the urine. For the purpose of this invention, it is important to distinguish that the acrolein metabolite of the oxazaphosphorines is associated with uroepithelial toxicity, and in contrast, cisplatin is associated with direct toxicity to the kidney (nephrotoxicity or renal toxicity).

Howell and colleagues (Howell et al., Intraperitoneal cisplatin with systemic thiosulfate protection, Ann. Int. Med., 97, 845–851, 1982) administered thiosulfates by intravenous infusion to cancer patients receiving intraperitoneal cisplatin. They observed that much higher (more than two fold) doses of cisplatin per meter square could be administered intraperitoneally and that renal toxicity could be prevented when thiosulfates are administered by the intravenous route. The inventors note that the use of sodium thiosulfate in an aqueous formulation of cis-diammine dichloro platinum is not medically practical because thiosulfate will inactivate cisplatin and are therefore incompatible in the same solution.

Protection against the nephrotoxicity of cisplatin in rats through mesna administration has not been established until the work of Kempf et al. As stated above, mesna disulfide is the only reported metabolite of mesna and mesna disulfide does not readily react with electrophilic alkylating agents such as nitrogen mustard or oxazaphosphorines (Brock et al., The development of mesna for the inhibition of urotoxic side effects of cyclophosphamide, ifosfamide, and other oxazaphosphorine anticancer drugs, Rec, Res. Cancer Res., 74, 270, 1980). After oral administration of mesna, the formation of dimesna reportedly occurs almost solely in the blood. One could surmise that intravascular dimesna would not react with cisplatin. After i.v. administration of mesna, the disulfide is reportedly spontaneously formed by autooxidation and found predominantly in the blood stream (Brock et al., Studies on the urotoxicity of oxazaphosphorine cytostatics and its prevention. Eur. J. Cancer. Clin. Oncol. 18, 1377, 1982). Brock and co-workers reported that dimesna is eliminated through the kidneys by glomerular filtration, and, to a great extent, reduced to mesna during excretion.

By additional per os administration of mesna, Kempf et al. demonstrated complete prevention of renal damage in rats after a single i.p. dose of 3 mg cisplatin/kg body weight. Their data demonstrated a clear dose/effect relationship, in that low doses of mesna only partially protected the kidneys of rats from renal damage.

The study of Kempf et al. notably involved the intraperitoneal administration of cisplatin with prior and subsequent oral administration of mesna in rats. The pharmacokinetics of intraperitoneally administered cisplatin differ substantially from the parenteral (e.g., intravenous) administration of cisplatin . In the case of intraperitoneal administration of cisplatin, it is possible to achieve much higher local (intraperitoneal) concentrations of cisplatin, and there is less risk of nephrotoxicity because cisplatin and its various species do not achieve similar peak plasma concentrations to those achieved with intravenous administration of cisplatin. Thus, at maximally tolerated dosages, the peak plasma concentration and the amount of cisplatin excreted by the kidney is less during intraperitoneal administration than the peak plasma concentration and amount of cisplatin excreted by the kidney when cisplatin is administered intravenously. Therefore, the experiments reported by Kempf et al. in rats fails to completely test the ability of concurrently administered parenteral dimesna in humans to protect against parenterally administered cisplatin . Second, the inventors contend that there is no art which teaches the simultaneous administration of dimesna to humans with any anticancer drug. Because of the above discussion, one could predict that the simultaneous administration of mesna would result in inactivation of cisplatin. The inventors further believe that the administration of mesna does not result in the formation of substantial amounts of dimesna in the plasma; rather mesna forms conjugates with other thiols, especially the amino acid cysteine which is abundant in the plasma (see above discussion). These mesna-thiol disulfide conjugates are subsequently excreted in the kidney. The mesna excreted or formed in the kidney can react with cisplatin.

Thus, this invention is novel because: (1) new art is described which takes into account the routes of administration of cisplatin and 2,2'-dithio-bis-ethane sulfonate (both are parenterally administered), (2) a novel method of use for both drugs involving the simultaneous parenteral administration of cisplatin and 2,2'-dithio-bis-ethane sulfonate is claimed, (3) new art is described which formulates 2,2'-dithio-bis-ethane sulfonate with cisplatin in a sterile aqueous formulation wherein this formulation is suitable for use in human subjects (or patients) with cancer, (4) the present invention presents a theory which overturns all previous reports and claims that oral or parenterally administered mesna undergoes autooxidation to form significant quantities of dimesna in the bloodstream of human subjects, (5) the present invention teaches that mesna forms disulfide linkages with cysteine as a free amino acid and in glutathione and homocysteine, and (6) the present invention teaches that disulfide linkage in 2,2'-dithio-bis-ethane sulfonate is chemically more labile than disulfide linkages found in mesna-cysteine or cysteine-cysteine molecules, and as such reduction of 2,2'-dithio-bis-ethane sulfonate yields greater free thiols than observed with the administration of mesna.

As stated above, this invention challenges the previous reports that mesna, to a large extent, forms dimesna in the plasma of humans. The inventors submit that oral or parenteral administration of mesna to human subjects results in the formation of more mesna-cysteine conjugates which are excreted by the kidney as compared to mesna-mesna conjugates. Cysteine, homocysteine and glutathione are endogenous thiols in human plasma and therefore could undergo reaction with mesna.

SUMMARY OF THE INVENTION

This invention provides a novel formulation containing both cis-diammine dichloro platinum and a water soluble disulfide, 2,2'-dithio-bis-ethane sulfonate in the same solution, wherein the presence of the disulfide and the parenteral administration of the formulation reduces the risk of cisplatin induced nephrotoxicity when treating human patients with cancer.

Thus, this invention teaches novel, aqueous, sterile parenteral formulations of cis-diammine dichloro platinum using the water soluble disulfide 2,2'-dithio-bis-ethane sulfonate for the purpose of treating patients with cancer and reducing the risk of cisplatin induced nephrotoxicity. This invention also teaches methods of manufacture and use of formulations containing cis-diammine dichloro platinum and disulfide 2,2'-dithio-bis-ethane sulfonate.

For the purposes of this invention, the simultaneous administration of cisplatin with 2,2'-dithio-bis-ethane sulfonate provides a physiologically safe source of additional sulfhydryl groups in the proximal and distal convoluted tubules to prevent renal toxicity. Unlike mesna, 2,2'-dithio-bis-ethane sulfonate is chemically inert with respect to cis-diammine dichloro platinum, and thus is compatible in the claimed formulation.

Concurrent administration of 2,2'-dithio-bis-ethane sulfonate with cisplatin is chemically and pharmacologically superior to using mesna because: (1) a greater amount of disulfides will be delivered to the renal tubular system whereupon these disulfides are available for reduction by glutathione reductase and thiol transferases to form the free thiol, 2-mercapto ethane sulfonate, and (2) a lower amount of energy is needed to reduce the 2,2'-dithio-bis-ethane sulfonate disulfide linkage which in turn will generate a greater amount of free thiols in the renal tubules whereupon these free thiols can react with the toxic aquo species of cisplatin.

This invention is also useful because the concurrent administration of 2,2'-dithiobis ethane sulfonate and cisplatin: (1) insures treatment compliance, (2) will reduce pharmacy preparation costs, (3) will reduce errors in prescribing both drugs, and (4) will reduce the amount of additional prophylactic maneuvers needed in order to reduce toxicity and avoid iatrogenic related complications (i.e. furosemide, or hypertonic saline administration as described above).

Also, the claimed invention will reduce cisplatin induced nephrotoxicity by the parenteral administration of both 2,2'-dithio-bis-ethane sulfonate and cis-diammine dichloro platinum. The 2,2'-dithio-bis-ethane sulfonate and cis-diammine dichloro platinum are in a sterile aqueous formulation suitable for administration to human subjects with cancer. Parenteral formulation of mesna (mercapto ethane sulfonate sodium) or sodium thiosulfate with cisplatin is not practical because the sulfhydryl groups on mesna or the sulfate anion of sodium thiosulfate will react with cisplatin yielding inactive species of cisplatin.

Formulations of cisplatin and 2,2'-dithio-bis-ethane sulfonate must be maintained at a pH less than 7.0 and greater than 1.0 because of the need to prevent the formation of aquo species of cisplatin and also to prevent the formation of mesna which could subsequently react with cisplatin species. Another important component of this invention is the use of sufficiently high concentrations of NaCl (e.g., 0.9% or greater) and HCl because the stability of cisplatin is proportionally related to the chloride ion concentration of the solution.

It is therefore the object of this invention to describe a novel formulation which contains both cis-diammine dichloro platinum and the water soluble disulfide, 2,2'-dithio-bis-ethane sulfonate, in the same formulation wherein the thiol reduces the risk of cisplatin induced nephrotoxicity when treating human patients with cancer.

For the purpose of this invention, "stable" means that the solution will not undergo major (>1%) chemical conversion within a reasonable period of time (dependent upon the final pH of the formulation mixture).

For the purpose of this invention, the word "about" when used for pH, cisplatin concentration, 2,2'-dithio-bis-ethane sulfonate concentration, NaCl concentration, or mannitol concentration is defined as +/−1%

For the purpose of this invention, there are numerous "anticancer agents" but the inventors prefer the following to be used with the claimed invention: 5-FU, bleomycin, VP-16 (etoposide), cyclophosphamide, ifosphamide, leucovorin, methotrexate, and vinblastine.

For the purpose of this invention, "amber vial" is any vial which protects the contents from exposure to fluorescent light.

One preferred embodiment of this invention is an injectable, sterile, stable aqueous solution which comprises cis-diammine dichloro platinum, 2,2'-dithio-bis-ethane sulfonate, sodium chloride and hydrochloric acid in a unit dosage form in a sealed container. This solution is suitable for intravenous administration to human patients with cancer by the injection thereof from the container. The following concentrations are included in the claimed injectable solution: the concentration of cis-diammine dichloro platinum is between about 0.1 mg/ml and about 1.0 mg/ml, the concentration of 2,2'-dithio-bis-ethane sulfonate is between 5 mg per ml to about 100 mg per ml by weight of water, the concentration of sodium chloride is between 0.9% and 3.0% by weight of water, and the hydrochloric acid is in an amount sufficient to maintain the pH in the range of 2.0 to 6.0.

Furthermore, this injectable solution can be given to a human patient with cancer who has not been treated with an anticancer agent (untreated) or this injectable solution can be given to a patient who has previously been treated or exposed to an anticancer agent(s). Also, this injectable solution can be administered to human patients with cancer in combination with another anticancer agent or agents. There are numerous "anticancer agents" but the inventors prefer the following to be used with the claimed invention: 5-FU, bleomycin, VP-16 (etoposide), cyclophosphamide, ifosphamide, leucovorin, methotrexate, and vinblastine.

Another embodiment of this invention is the addition of mannitol in a concentration between about 1.0% to about 1.5% by weight of water to the above disclosed injectable solution.

Yet another embodiment of this invention is an injectable, sterile, aqueous solution consisting essentially of (a) cis-diammine dichloro platinum in a concentration between about 0.1 mg per ml and about 1.0 mg per ml by weight of water; (b) 2,2'-dithio-bis-ethane sulfonate in a concentration between 5 mg per ml to about 100 mg per ml by weight of water; (c) sodium chloride at a concentration of 0.9% to 3.0% by weight of water; (d) mannitol in a concentration of between about 1.0% to about 1.5% by weight of water; and (e) a pH in the range of 2.0 to 6.0 wherein the pH range is achieved by adding hydrochloric acid. Also, for this invention, components (a) through (e) are in a unit dosage form in a sealed container. Additionally, this claimed solution is suitable for intravenous administration to untreated or previously treated human patients with cancer by the injection thereof from the container.

Furthermore, this injectable solution can be given to a human patient with cancer who has not been treated with an anticancer agent (untreated) or this injectable solution can be given to a patient who has previously been treated or exposed to an anticancer agent(s). Also, this injectable solution can be administered to human patients with cancer in combination with another anticancer agent or agents. There are numerous "anticancer agents" but the inventors prefer the following to be used with the claimed invention: 5-FU, bleomycin, VP-16 (etoposide), cyclophosphamide, ifosphamide, leucovorin, methotrexate, and vinblastine.

DETAILED DESCRIPTION OF THE PREFERRED EMBODIMENTS

Figure 1A:
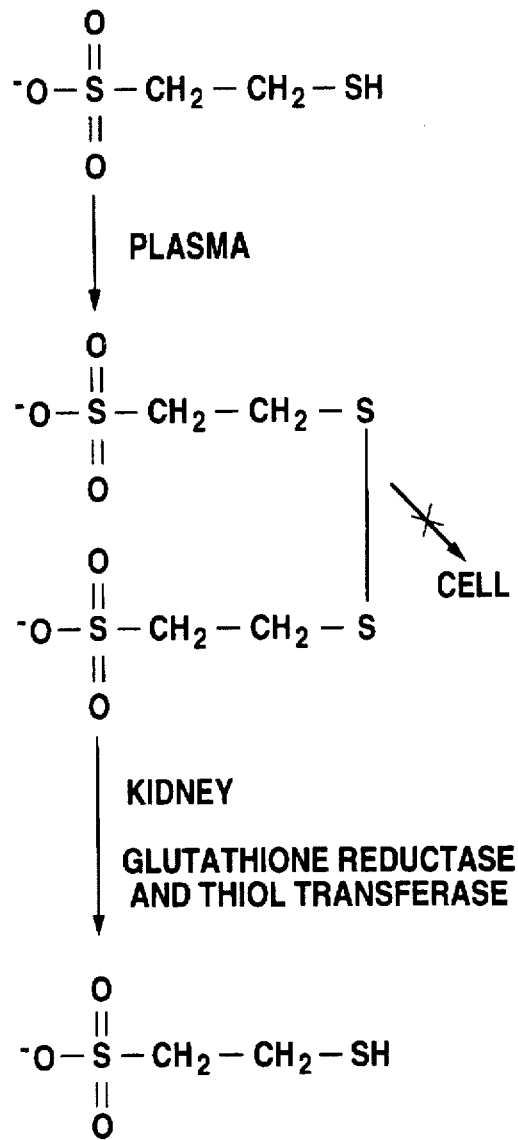
FIG. 1. Comparative Human Pharmacology and Metabolism of 2-Mercapto Ethane Sulfonate (Mesna) and 2,2'-Dithio-Bis-Ethane Sulfonate.
Figure 1B:
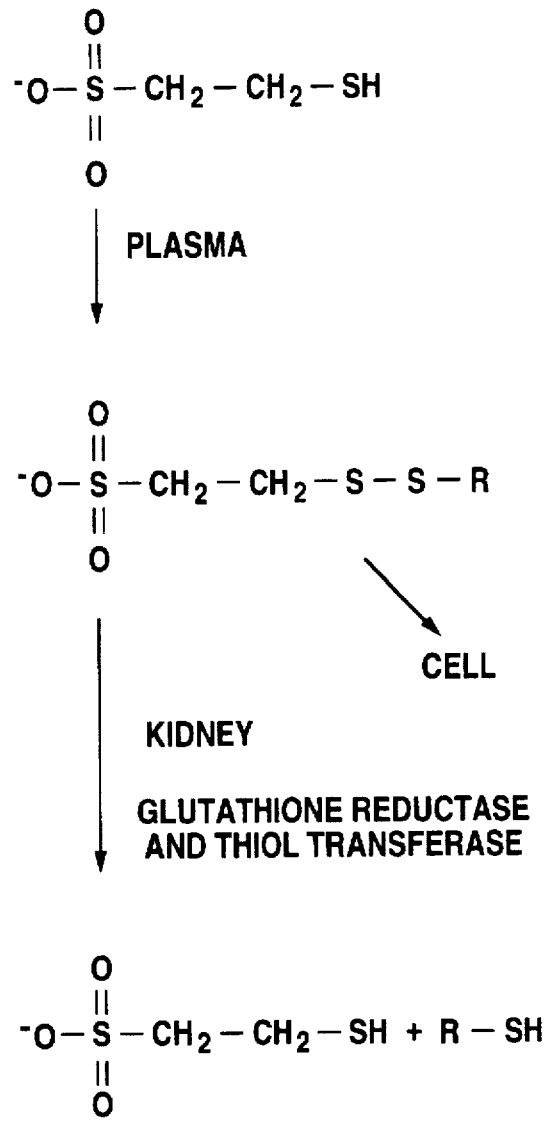
Figure 1C:
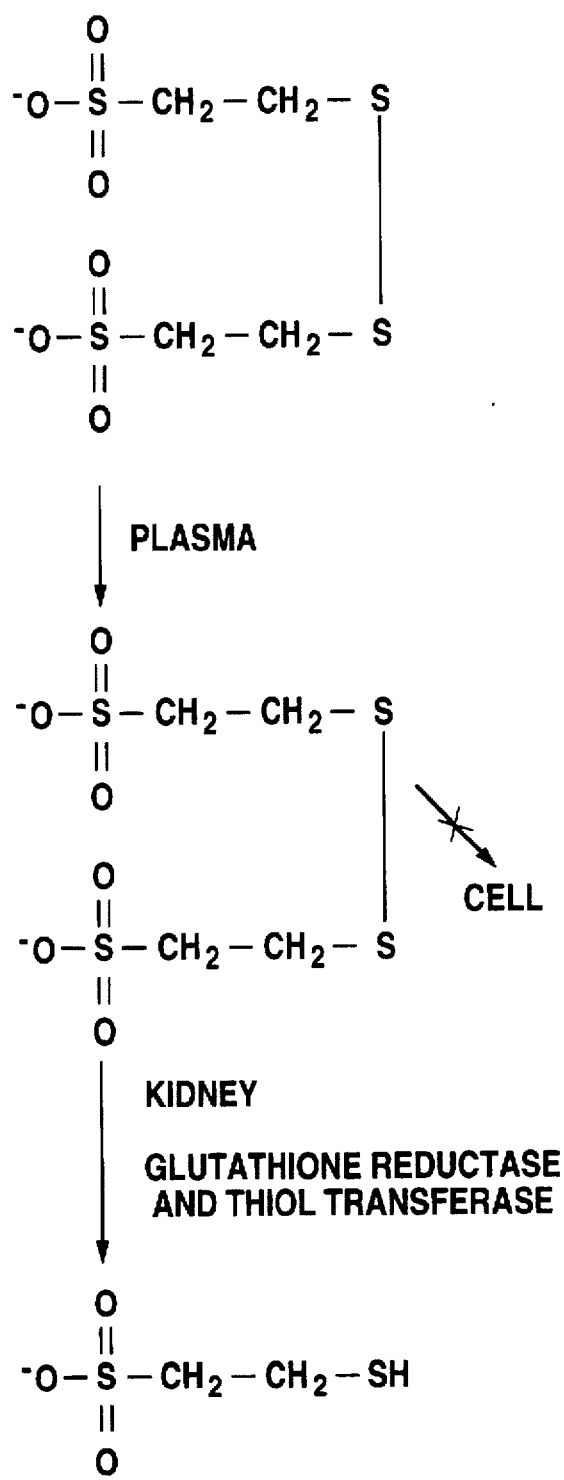

In its preferred embodiments, this invention involves the preparation and administration of a sterile, aqueous formulation of cis-diammine dichloro platinum with 2,2'-dithio-bis-ethane sulfonate in the same formulation.

EXAMPLES

The following examples illustrate selected modes for carrying out the claimed invention and are not meant to be construed as limiting the specification and claims in any way.

EXAMPLE 1

Preparation of 2,2'-Dithio-bis-ethane Sulfonate 2,2'-Dithio-bis-ethane sulfonate is prepared by oxidizing 2-mercapto ethane sulfonate in water with equimolar amount of iodine as previously reported by Lamaire and Reiger (Lemaire and Reiger, J. Org. Chem., 26, 1330–1, 1961).

EXAMPLE 2

Stability of 2,2'-Dithio-bis-ethane Sulfonate

The stability of 2,2'-dithio-bis-ethane sulfonate at room temperature was determined at pH ranges of 1.5 to 9.0 2,2'-Dithio-bis-ethane sulfonate, as produced by the method described above, was found to be stable in the pH range of 1.5–9.0.

Briefly, the following experiment was performed to determine the stability of 2,2'-dithio-bis-ethane sulfonate in acidic and basic aqueous media. In a typical experiment, 50 mg of 2,2'dithio-bis-ethane sulfonate (as produced by using the above described method) was dissolved in one ml of water and the pH was adjusted to 1.5, 2.0, 3.0, 4.0, 5.0 or 6.0 by adding 1N hydrochloric acid in water or the pH was adjusted to 8.0 or 9.0 by adding 1N sodium hydroxide in water. The reaction mixture was stirred for 24 hours at room temperature, the water was removed at reduced pressure, dissolved in spectral grade $D_2O$, and the proton NMR spectrum was recorded. One peak corresponding to the starting material was observed on the NMR spectra; no additional peaks were observed.

The stability of 2,2'-dithio-bis-ethane sulfonate at pH 1.5 was further studied by heating the reaction mixture to 100 degrees Centigrade for 10 minutes. No change in the proton spectrum was observed after heating the 2,2'-dithio-bis-ethane sulfonate (pH 1.5). The data indicate that 2,2'-dithio-bis-ethane sulfonate is stable in aqueous solutions at pH values from 1.5 to 9.0.

EXAMPLE 3

Method #1 to Produce a Sterile Solution Containing Cisplatin and 2,2'-Dithio-bis-ethane Sulfonate This example is designed to detail one method to produce a sterile solution containing cisplatin and disodium 2,2'-dithio-bis-ethane sulfonate. For the purpose of this example, cisplatin and cis-diammine dichloro platinum are used interchangeably. For the purpose of this example, "approximately" is defined to include a range of plus or minus 1%.

Step 1. U.S.P. grade of sodium chloride (NaCl; purchased from VWR Scientific) is dissolved in sterile, injectable water to a final concentration of 0.9% NaCl by weight of water. A suitable amount of pure hydrochloric acid (HCl, 99.999%; purchased from Aldrich Chemical Company) is added to the sterile, injectable 0.9% sodium chloride solution in order to obtain a final pH in the range of approximately 2.0 to 6.0.

Step 2. One part by weight of pure, cisplatin (99.999%, purchased from Aldrich Chemical Company) is added to the admixture of Step 1. The cisplatin is allowed to completely dissolve by agitation (1500–2500 rpm) at room temperature, for 60 to 90 minutes.

Step 3. Then, 15 parts by weight of disodium 2,2'-dithio-bis-ethane sulfonate (as produced above in Example 1) is added the mixture of Step 2. This mixture is agitated until complete dissolution and the final pH is adjusted to a pH ranging between approximately pH 2.0 and pH 6.0 by adding pure hydrochloric acid (99.999%, purchased from Aldrich Chemical Company).

Step 4. The solution of Step 3 is sterilized via filtration through a sterile 0.22 micron filter (obtained from VWR Scientific).

Step 5. The sterile solution of Step 4 is stored in sterile injection amber vials wherein each vial contains approximately 0.9 mg of cisplatin and 14.3 mg of 2,2'-dithio-bis-ethane sulfonate per ml of injection solution.

EXAMPLE 4

Method #2 to Produce a Sterile Solution Containing Cisplatin and 2,2'-Dithio-bis-ethane Sulfonate This example is designed to detail another method to produce a sterile solution containing cisplatin and disodium 2,2'-dithio-bis-ethane sulfonate. For the purpose of this example, cisplatin and cis-diammine dichloro platinum are used interchangeably. For the purpose of this example, "approximately" is defined to include a range of plus minus 1%.

Step 1. U.S.P. grade of sodium chloride (NaCl; purchased from VWR Scientific) is dissolved in sterile, injectable water to a final concentration of 0.9% NaCl by weight of water.

Step 2. Disodium 2,2'-dithio-bis-ethane sulfonate (as produced above in Example 1; fifteen (15) parts by weight) is added to the sterile, injectable 0.9% NaCl solution from Step 1. The 2,2'-dithio-bis-ethane sulfonate is allowed to completely dissolve by agitation (1500–2500 rpm) at room temperature. This should take 5–10 minutes at room temperature. The pH of the 2,2'-dithio-bis-ethane sulfonate solution is adjusted to a pH ranging between approximately pH 2.0 and pH 6.0 by adding pure (99.999% purity) hydrochloric acid.

Step 3. Cisplatin (99.999% purity; purchased from Aldrich Chemical Company) is added (1 part by weight) to the solution of Step 2. This mixture is agitated until complete dissolution and the final pH is adjusted to a pH ranging between approximately pH 2.0 and pH 6.0 by adding pure (99.999% purity) hydrochloric acid.

Step 4. The solution of Step 3 is sterilized via filtration through a sterile 0.22 micron filter (obtained from VWR Scientific).

Step 5. The sterile solution of Step 4 is stored in sterile injection amber vials wherein each vial contains approximately 1.0 mg of cisplatin and 14.3 mg of 2,2'-dithio-bis-ethane sulfonate per ml of injection solution.

EXAMPLE 5

Method #3 to Produce a Sterile Solution Containing Cisplatin and 2,2'-Dithio-bis-ethane Sulfonate This example is designed to detail another method to produce a sterile solution containing cisplatin and disodium 2,2'-dithio-bis-ethane sulfonate. For the purpose of this example, cisplatin and cis-diammine dichloro platinum are used interchangeably. For the purpose of this example, "approximately" is defined to include a range of plus or minus 1%.

Step 1. A suitable amount of pure, disodium 2,2'-dithio-bis-ethane sulfonate (as produced in Example 1) is dissolved in sterile, injectable water to a concentration of 15.0 mg/ml.

Step 2. U.S.P. grade sodium chloride crystals (NaCl; purchased from VWR Scientific) is added to the solution of Step 1 such that the final concentration of NaCl is 0.9% by weight of water.

Step 3. The pH of the 2,2'-dithio-bis-ethane sulfonate—NaCl solution of Step 2 is adjusted to range between approximately pH 2.0 and pH 6.0 by the addition of pure (99.999% purity), hydrochloric acid (purchased from Aldrich Chemical Company).

Step 4. An amount of cisplatin (99.999% purity; purchased from Aldrich Chemical Company) is added to the solution of Step 3 such that the final concentration is approximately 1.0 mg/ml cisplatin.

Step 5. The solution of Step 4 is sterilized via filtration through a sterile 0.22 micron filter.

Step 6. The sterile solution of Step 5 is store in sterile injection amber vials wherein each vial contains approximately 1.0 mg of cisplatin and 14.3 mg of 2,2'-dithio-bis-ethane sulfonate per ml of injection solution.

EXAMPLE 6

Method #4 to Produce a Sterile Solution Containing Cisplatin and 2,2'-Dithio-bis-ethane Sulfonate This example is designed to detail another method to produce a sterile solution containing cisplatin and disodium 2,2'-dithio-bis-ethane sulfonate. For the purpose of this example, cisplatin and cis-diammine dichloro platinum are used interchangeably. For the purpose of this example, "approximately" is defined to include a range of plus or minus 1%.

Step 1. U.S.P. grade sodium chloride (NaCl; purchased from VWR Scientific) is dissolved in sterile, injectable water to a final concentration of 0.9% NaCl by weight of water.

Step 2. The pH of this NaCl solution is brought to approximately 2.0 to 6.0 by the addition of 99.999% pure hydrochloric acid (purchased from Aldrich Chemical Company).

Step 3. Suitable amount of cisplatin (99.999% purity; purchased from Aldrich Chemical Company) is added to the solution obtained in Step 2 and allowed to dissolve completely by agitation (1500–2500 rpm) for approximately 60 to 90 minutes at room temperature.

Step 4. Then, 30 parts by weight of disodium 2,2'-dithio-bis-ethane sulfonate (as produced in Example 1) is added to the solution Step 3. The 2,2'-dithio-bis-ethane sulfonate-cisplatin mixture is allowed to completely dissolve with agitation at room temperature.

Step 5. The pH of the disodium 2,2'-dithio-bis-ethane sulfonate—cisplatin solution is adjusted to a final pH ranging between approximately 2.0 and 6.0 by the addition of pure (99.999% purity) hydrochloric acid (obtained from Aldrich Chemical Company).

Step 6. The solution of Step 5 is sterilized via filtration through a sterile 0.22 micron filter (obtained from VWR Scientific)

Step 7. The sterile solution of Step 6 is stored in sterile injection amber vials wherein each vial contains 0.5 mg of cisplatin and 12.9 mg of 2,2'-dithio-bis-ethane sulfonate per ml of injection solution.

EXAMPLE 7

Method #5 to Produce a Sterile Solution Containing Cisplatin and 2,2'-Dithio-bis-ethane Sulfonate This example is designed to detail another method to produce a sterile solution containing cisplatin and disodium 2,2'-dithio-bis-ethane sulfonate. For the purpose of this example, cisplatin and cis-diammine dichloro platinum are used interchangeably. For the purpose of this example, "approximately" is defined to include a range of plus or minus 1%.

Step 1. U.S.P. grade sodium chloride (NaCl; purchased from VWR Scientific) is dissolved in sterile, injectable water to a final concentration of 0.9% NaCl by weight of water.

Step 2. An amount of pure (99.999% purity) hydrochloric acid (obtained from Aldrich Chemical Company) is added to the NaCl solution of Step 1 in order to obtain a final pH in the range of approximately 2.0 to 6.0.

Step 3. An amount of U.S.P. grade potassium chloride crystals (KCl; purchased from VWR Scientific) is dissolved in the solution of Step 2 (0.9% NaCl) such that the final concentration of potassium chloride is 0.1% by weight.

Step 4. One part by weight of cisplatin (99.999% purity; purchased from Aldrich Chemical Company) is added to the solution of Step 3 and is completely dissolved by agitation (1500 to 2500 rpm) for approximately 60 to 90 minutes at room temperature.

Step 5. Thirty (30) parts by weight of disodium 2,2'-dithio-bis-ethane sulfonate (as produced by Example 1) is added to the solution of Step 4. This mixture is agitated until complete dissolution and the final pH ranging between approximately pH 2.0 and pH 6.0 by adding pure (99.999% purity) hydrochloric acid (purchased from Aldrich Chemical Company).

Step 6. The solution of Step 5 is sterilized via filtration through a sterile 0.22 micron filter (obtained from VWR Scientific)

Step 7. The sterile solution of Step 6 is stored in sterile injection amber vials wherein each vial contains approximately 1.0 mg of cisplatin and 28.7 mg of 2,2'-dithio-bis-ethane sulfonate per ml of injection solution.

EXAMPLE 8

Method #6 to Produce a Sterile Solution Containing Cisplatin and 2,2'-Dithio-bis-ethane Sulfonate This example is designed to detail another method to produce a sterile solution containing cisplatin and disodium 2,2'-dithio-bis-ethane sulfonate. For the purpose of this example, cisplatin and cis-diammine dichloro platinum are used interchangeably. For the purpose of this example, "approximately" is defined to include a range of plus or minus 1%.

Step 1. U.S.P. grade sodium chloride (NaCl; purchased from VWR Scientific) is dissolved in sterile, injectable water to a final concentration of 0.9% NaCl by weight of water. A suitable amount of pure (99.999% purity) hydrochloric acid is added to the sterile, injectable 0.9% sodium chloride solution in order to obtain a final pH in the range of approximately 2.0 to 6.0.

Step 2. Pure mannitol (99+% purity, purchased from Aldrich Chemical Company) is dissolved in the solution of Step 1 so that the concentration of mannitol is 1.0% by weight.

Step 3. One part by weight cisplatin (purchased from Aldrich Chemical Company, 99.999% purity) is added to the admixture of Step 2. The cisplatin is allowed to completely dissolve by agitation (1500–2500 rpm) at room temperature (approximately 60 to 90 minutes).

Step 4. Then, 30 parts by weight of disodium 2,2'-dithio-bis-ethane sulfonate (as produced in Example 1) is added to the mixture of Step 3. This mixture is agitated until complete dissolution and the final pH is adjusted to a pH ranging between approximately pH 2.0 and pH 6.0 by adding pure (99.999% purity) hydrochloric acid (purchased from Aldrich Chemical Company).

Step 5. The solution of Step 4 is sterilized via filtration through a 0.22 micron filter (obtained from VWR Scientific).

Step 6. The sterile solution of Step 5 is stored in sterile injection amber vials wherein each vial contains approximately 0.5 mg of cisplatin and 12.9 mg of 2,2'-dithio-bis-ethane sulfonate per ml of injection solution.

EXAMPLE 9

Stability of 2,2'-Dithio-bis-ethane Sulfonate and Cisplatin Formulations

This example is designed to study the stability of 2,2'-dithio-bis-ethane sulfonate and cisplatin formulations.

1. First, 2,2'-dithio-bis-ethane sulfonate—cisplatin formulations will be prepared according to Examples 3 through 8.
2. The final pH of each formulation will be adjusted to a range of 2.0 to 6.0.
3. Each pH adjusted 2,2'-dithio-bis-ethane sulfonate—cisplatin formulation will be stored in a sealed glass vial protected from fluorescent light at room temperature (approximately 27+or −2 degrees Celsius.).
4. The stability of each pH adjusted 2,2'-dithio-bis-ethane sulfonate—cisplatin formulation will be analyzed on a weekly basis for at least 6 (six) months by nuclear magnetic resonance (NMR) analysis. The NMR spectra will be compared to a freshly prepared and pH adjusted 2,2'-dithio-bis-ethane sulfonate—cisplatin formulation. Observing one peak corresponding to the freshly prepared formulation will denote stability of the pH adjusted formulation over time, as a function of pH.

REFERENCES

Arrick, B. A., et al., Glutathione metabolism as a determinant of therapeutic efficacy: A review. Cancer Res. 44:4224, 1984.

Andrews, P. A., et al., Metallothionein-mediated cisplatin resistance in human ovarian carcinoma cells. Cancer Chemother. Pharmacol., 19:149, 1987.

Bajorin, D. F., et al., Pharmacokinetics of cis-diamminedichloroplatinum (II) after administration in hypertonic saline. Cancer Res. 46:5969, 1986.

Borch, R. F., et al., Effect of diethyldithiocarbamate rescue on tumor response to cisplatinum in a rat model Proc. Natl. Acad. Sci. USA., 77:5441, 1980.

Brock, N., et al., Studies on the Urotoxicity of Oxazaphosphorine Cytostatics and its Prevention, Eur. J. Cancer Clin. Oncol., 17:1155–1163, 1981

Brock, N., et al., Studies on the Urotoxicity of Oxazaphosphorine Cytostatics and its Prevention-III. Profile of Action of Sodium 2-mercaptoethane Sulfonate (Mesna). Eur J. Cancer Clin. Oncol. 18(12): 1377–1387, 1982.

Brock, N., et al. Arzneim Forsch 32:486–487 (1982).

Brock, N., et al., Pharmacokinetics and Mechanism of Action of Detoxifying Low-Molecular-Weight Thiols. J Cancer Res. Clin. Oncol. 108:87–97, 1984.

Brock, N. and Pohl, J. The development of mesna for regional detoxification. Cancer Treat. Rev. 10(Suppl. A):33 (1983).

Burkert, H., et al., Clinical Overview of Mesna. Cancer Treatment Reviews. 10 (Supplement A): 175–181, 1983.

Burkert, H., et al., Bioavailability of Orally Administered Mesna. Arzneim.-Forsch./Drug Res. 34:(11), 1597, 1984.

Campbell, A. B., et al., Plasma platinum levels: Relationship to cisplatin dose and nephrotoxicity. Cancer Treat. Rep., 67, 169, 1983.

Choie, D. D., et al., Acute and chronic cisplatin nephropathy in rats. Lab. Invest., 44, 397, 1981.

Daugaard, G., et al., Cisplatin toxicity A review. Cancer Chemother. Pharmacol. 25:1, 1989.

DeConti, R. C., et al., Clinical and pharmacological studies with cis-diammine dichloro platinum (II). Cancer Res., 33:1310, 1973.

Dentino, M., et al., Long term effect of cis-diamminedichloroplatinum(CDDP) on renal function and structure in man. Cancer, 41:1274, 1978.

Earhart, R. H., Instability of cis-dichlorodiammine platinum in dextrose solution. Cancer Treat. Rep., 62:1105, 1978.

Eastman, A., Glutathione-mediated activation of anticancer platinum (IV) complexes. Biochem. Pharmacol. 36:4177, 1987.

Eastman, A., Reevaluation of interaction of cis-dichloro (ethylenediamine) platinum (II) with DNA. Biochemistry, 25:3912, 1986.

Glover, D., et al., WR-2721 and high-dose cisplatin: An active combination in the treatment of metastatic melanoma. J. Clin. Oncol. 5:574, 1987.

Goldstein, R. S., et al., The nephrotoxicity of cisplatin. Life Sci., 32, 685, 1983.

Gonzalez-Vitale, J. C., et al., The renal-pathology in clinical trials of cisplatin (II) diamminedichloride. Cancer, 39, 1362, 1977.

Hayes, D. M., et al., High dose cisplatin diammine dichloride, amelioration of renal toxicity by mannitol diuresis. Cancer, 39, 1372, 1977.

Howell, S. B., Intraperitoneal cisplatin with systemic thiosulfate protection, Ann. Int. Med., 97, 845–851, 1982.

Hegedus, L., et al., Chemical reactivity of cisplatin bound to plasma proteins. Cancer Chemother. Pharmacol., 20:211, 1987.

Jacobs, C., et al., Renal handling of cis-diamminedichloroplatinum (II). Cancer Treat. Rep., 64:1223, 1980.

James, C. A. and Rogers, H.J., Estimation of mesna and dimesna in plasma and urine by high performance liquid chromatography with electrochemical detection, Journal of Chromatography, 382, 394–398, 1986.

Jocelyn, Biochemistry of the SH Group, Academic Press, London, N.Y., 1972.

Kelley, S. L., et al., Overexpression of metallothionein confers resistance to anticancer drugs. Science, 241:1813, 1988.

Kempf, S. R., et al., Effective prevention of the nephrotoxicity of cisplatin (CDDP) by administration of sodium 2-mercaptoethane-sulfonate (mesna) in rats. Br. J. Cancer, 52:937–939, 1985.

Kociba, R. J., et al., Acute toxicologic and pathologic effects of cis-diammine-dichloro-platinum in the male rat. Cancer Chemother. Rep., 55, 1, 1971.

Lemaire, L. and Reiger, M., Synthesis of 2-mercaptoethane sulfonamide, J. Org. Chem. 26, 1330–1, 1961.

Markman, M.: Intraperitoneal chemotherapy. Semin. Oncol. 18:248, 1991.

Leonard, B. J., et al., Antileukemic and nephrotoxic properties of platinum compounds. Nature, 234:43, 1971.

Offerman, J. J. G., et al., Acute effects of cis-diamminedichloroplatinum (CDDP) on renalfunction. Cancer Chemother. Pharmacol., 12, 36, 1984.

Ormstad et al., Cancer Research, 43:333, 1983.

Ostrow, S., et al., High-dose cisplatin therapy using mannitol versus furosemide diuresis: comparative pharmacokinetics and toxicity. Cancer Treat. Rep., 65, 73, 1981.

Ozols, R. F., et al., High-dose cisplatin in hypertonic saline. Ann. Intern. Med., 100, 19, 1984.

Pfeifle, C. E., et al., High-dose cisplatin with sodium thiosulfate protection. J. Clin. Oncol., 3:237, 1985.

Pinto, A. L., et al., Binding of the antitumour drug cis-diamminedichloroplatinum(II) (cisplatin) to DNA. Biochim. Biophys. Acta. 780:167, 1985.

Pohl, et al. Meth. Find. Clin. Pharmacol. 3(Suppl 1):95–101, 1981.

Perry, M. C., The Chemotherapy Source Book, Williams and Wilkins, 1172 pp., 1992.

Reed, E., et al., "Platinum analogues, " in Cancer Chemotherapy. Principles and Practice, 465–490, 1990.

Rosenberg, B., et al., Platinum compounds: A new class of potent antitumor agents. Nature 222:385, 1969.

Rozenzweig, M., et al., cis-diamminedichloroplatinum (II). Ann. Intern. Med., 86, 803, 1977.

Safirstein, R., et al., Cisplatin nephrotoxicity. Am. J. Kidney Dis. 8:356, 1986.

Sidau, B. and Shaw, I .C., Determination of sodium 2-mercaptoethane sulfonate by high performance liquid chromatography using post-column reaction calorimetry or electrochemical detection, Journal of Chromatography, 311, 234–238, 1984.

Symposium: Cisplatin: contemporary treatment approaches. Semin. Oncol. 16 (Suppl. 6):1–128, 1989.

Thompson, A. J., The Interactions of platinum compounds with biological molecules. Rec. Res. Cancer Res. 48:38, 1974.

The foregoing description has been directed to particular embodiments of the invention in accordance with the requirements of the Patent Statues for the purposes of illustration and explanation. It will be apparent, however, to those skilled in this art, that many modifications, changes, and variations in the claimed solutions and methods set forth will be possible without departing from the scope and spirit of the claimed invention. It is intended that the following claims be interpreted to embrace all such modifications, variations, and changes.

What is claimed is:

1. An injectable, sterile, stable aqueous solution consisting of cis-diammine dichloro platinum, 2,2'-dithio-bis-ethane sulfonate, sodium chloride and hydrochloric acid in a unit dosage form in a sealed container, wherein said solution is suitable for intravenous administration to human patients with cancer by the injection thereof from said container, wherein said concentration of cis-diammine dichloro platinum is between about 0.1 mg/ml and about 1.0 mg/ml, wherein said concentration of 2,2'-dithio-bis-ethane sulfonate is between about 5 mg per ml and about 100 mg per ml by weight of water, wherein said concentration of sodium chloride is between about 0.9% and about 3.0% by weight of water, and wherein said hydrochloric acid is in an amount sufficient to maintain the pH in the range of 2.0 to 6.0.

2. The injectable solution of claim 1 further consisting of mannitol in a concentration between about 1.0% and about 1.5% by weight of water.

3. The injectable solution of claim 2 wherein said solution is administered to human patients with cancer in combination with another anticancer agent or agents selected from the group consisting of 5-FU (5-Fluorouracil), bleomycin, VP-16 (etoposide), cyclophosphamide, ifosphamide, leucovorin, methotrexate, and vinblastine.

* * * * *